United States Patent [19]

Goldenberg

[11] Patent Number: 5,739,755
[45] Date of Patent: Apr. 14, 1998

[54] SENSOR FOR MONITORING THE COOLING LIQUID OF HEAT EXCHANGER CIRCUITS

[75] Inventor: Emanuel Goldenberg, Poissy, France

[73] Assignee: Institut Francais du Petrole, Rueil Malmaison, France

[21] Appl. No.: 619,191

[22] Filed: Mar. 21, 1996

[30] Foreign Application Priority Data

Mar. 21, 1995 [FR] France .................................. 95 03387

[51] Int. Cl.[6] .................................................. G08B 21/00
[52] U.S. Cl. ........................ 340/627; 340/590; 116/268; 116/272
[58] Field of Search .................................. 340/627, 591, 340/590, 614; 200/61.04, 83.1; 123/41.15; 73/307; 137/67; 116/272, 268; 165/11.1

[56] References Cited

U.S. PATENT DOCUMENTS

| 3,068,831 | 12/1962 | Witchell | 116/272 |
|---|---|---|---|
| 3,402,690 | 9/1968 | Willis | 116/272 |
| 4,147,596 | 4/1979 | Baboian et al. | 123/41.15 |
| 4,306,127 | 12/1981 | Payne | 200/61.04 |
| 4,313,042 | 1/1982 | Ehrhart | 200/61.04 |
| 4,325,059 | 4/1982 | Jaye | 340/590 |
| 4,745,876 | 5/1988 | Whiting | 116/268 |
| 5,181,536 | 1/1993 | Argyle et al. | 165/11.1 |
| 5,339,764 | 8/1994 | Singbartl | 116/272 |

FOREIGN PATENT DOCUMENTS

| 1076864 | 5/1980 | Canada. |
|---|---|---|
| 0511880 | 11/1992 | European Pat. Off.. |
| 2689240 | 10/1993 | France. |
| 91/16614 | 10/1991 | WIPO. |

*Primary Examiner*—Jeffery Hofsass
*Assistant Examiner*—John Tweel, Jr.
*Attorney, Agent, or Firm*—Antonelli, Terry, Stout, & Karus, LLP

[57] ABSTRACT

A sensor for monitoring a cooling liquid circulating in a circuit of a heat exchanger of an automobile, for example, includes a support for mounting the sensor on a pipe of the circuit so that the liquid is in contact with at least a part of the sensor, a corrodible membrane in contact with the liquid, and a visual indicator reacting to the degree of corrosion of the liquid. The visual indicator includes a piston movable under the combined effect of the breaking of the corrodible membrane and of the pressure difference between inside and outside of the pipe, at least one seal mounted on the movable piston, and the visual indicator protruding from the pipe and/or from the support when the membrane is corroded.

7 Claims, 1 Drawing Sheet

SENSOR FOR MONITORING THE COOLING LIQUID OF HEAT EXCHANGER CIRCUITS

FIELD OF THE INVENTION

The present invention relates to the field of in-situ monitoring of cooling fluids circulating in heat exchangers, and more particularly to the monitoring of their corrosion level.

The present invention can preferably be used to monitor at what time the cooling liquid circulating in internal-combustion engines becomes corrosive.

BACKGROUND OF THE INVENTION

It is well-known that, in an internal-combustion engine, the cooling liquid, besides its heat exchange function, also allows to protect the cooling circuit of the engine against the main forms of degradation to which it is subjected. Pit corrosion, metal tearing by cavitation, electrochemical corrosion . . . are the most encountered forms of degradation which, if they are not detected soon enough, are likely to cause considerable disruptions or even damages to the engine.

In order to fulfil this protective function, cooling liquids therefore require a particularly well-designed formulation. They contain additives intended to protect the different metals of the cooling circuit.

However, during operation, the formulation of the cooling liquid can change through the decomposition or the impoverishment of some additives.

This change poses problems because cooling liquid can then degrade certain materials of the circuit.

It is currently necessary to replace periodically and arbitrarily the cooling liquid in order to avoid attacks on the circuit such as those described above.

Among the known detection and monitoring systems of connected application, U.S. Pat. No. 4,792,791 discloses a device intended to monitor the quality of the lubricating oil of an engine thanks to the corrosion of a resistive element belonging to an electric circuit.

When the resistive element is corroded by the oil in which it is immersed, its resistance varies, then this variation is recorded and considered to be a sign of aging of the oil.

Exploitation of the resistance variation of a corrodible sensitive element is also disclosed in U.S. Pat. Nos. 4,675,662, and 4,782,332 or in patent application FR-2,689,240 filed in the name of the applicant.

Although such systems are satisfactory since they allow to monitor the aging of an oil or of another liquid necessary for the running of the engine, they only react when the liquid is in a rather advanced state of degradation or aging.

There is also a well-known device for monitoring the aging of cooling fluids circulating in heat exchangers, comprising an element in contact with said liquid, an electric element separated from the element in contact with the liquid by an isolating volume containing a fluid at atmospheric pressure, said electric element reacting to the degree of corrosion of the element in contact, and an alarm reacting to a variation of the signal of the electric element. According to this document, the element in contact with the liquid to be monitored consists of at least one chip made up of a material that is also in contact with the liquid in the circuit. The electric element is here a piezoelectric element whose frequency varies with a pressure variation in the isolating volume.

Beside this prior art, there is a need for a simpler, less costly and also more reliable sensor that could for example be mounted in heavy-duty vehicles, directly on the engine. A mechanical system based on a visual indication can then come up to this expectation.

SUMMARY OF THE INVENTION

To that effect, the present invention proposes a sensor for monitoring the cooling liquid circulating in a circuit of a heat exchanger comprising:

a support intended to mount the sensor on a pipe of the circuit, so that said liquid is in contact with at least part of the sensor, a corrodible membrane in contact with the liquid, a visual indicator reacting to the degree of corrosion of the liquid.

According to the invention, the visual indicator includes a means movable under the combined effect of the breaking of the corrodible membrane and of the pressure difference between the inside and the outside of the pipe, at least one seal means mounted on the means, the visual indicator protruding from the pipe and/or the support when said membrane is corroded.

According to one if its characteristics, the movable means is at least partly covered externally with a coloured film.

The movable means preferably comprises a magnetized zone and the sensor also includes a contactor placed outside the pipe, co-operating with the magnetized zone and belonging to an electric circuit allowing an alarm to be activated when the magnetized zone is opposite the contactor.

Furthermore, the sensor according to the invention can include a second seal means intended to prevent dust from getting into the sensor and from hampering the motion of the movable means.

According to a particular embodiment of the invention, the movable means includes a piston housed and sliding in said support.

The second seal means can be an O-ring mounted on the piston.

According to another embodiment of the invention, the piston has a pointed end and the second seal means is a membrane covering the opening of the piston housing, that can be pierced by the pointed end of the piston when the latter moves towards the outside of the pipe and/or of the support.

The present invention thus allows a visual indication that can be given either by a mechanical device or through an electric circuit. The two means can be present simultaneously or separately.

BRIEF DESCRIPTION OF THE DRAWINGS

Other features, advantages and details of the present invention will be clear from reading the description hereafter, given by way of non limitative examples, with reference to the accompanying drawings in which.

DESCRIPTION OF THE PREFERRED EMBODIMENTS

Figure 1:
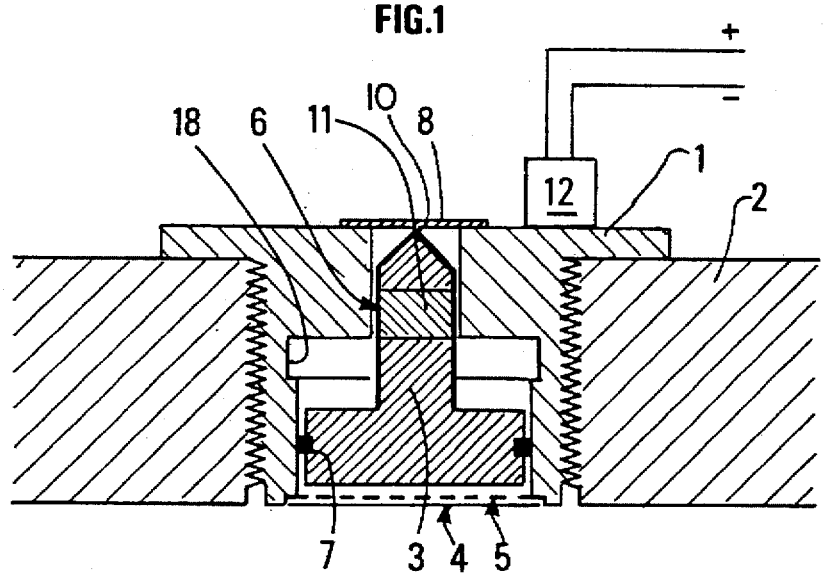
FIG. 1 is a longitudinal section of an embodiment of the invention.

According to FIG. 1, the sensor comprises a support 1 screwed or fastened by any means known in the art to the wall 2 of a pipe in which the fluid to be monitored circulates.

The sensor according to the invention is preferably mounted in a bend of the circuit, where the velocity of the fluid is the highest.

Support 1 is internally provided with a housing for a means such as a piston 3 movable between two positions, as explained hereafter.

A corrodible membrane 4 in contact with the liquid to be monitored is fastened to support 1.

A support-grid 5 can optionally be fastened to support 1, behind the corrodible membrane, so as to prevent untimely displacements of piston 3 or the tearing of corrodible membrane 4 under the sole effect of the pressure in the circuit.

Besides, support-grid 5 can form a stop for piston 3 and prevent it from being driven towards the inside of the pipe.

It is desirable that piston 3 be placed originally as close as possible to support-grid 5.

The piston can thus no longer return to its initial position once it has moved out of its housing, even if an underpressure occurs in the pipe. Any other means preventing the piston from returning to its initial position can of course be contemplated without departing from the scope of the present invention.

Furthermore, at least part of piston 3 is preferably covered with a coloured film 6 intended to catch the eye when the liquid to be monitored is corroded.

A seal element such as an O-ring 7 is mounted on piston 3 in order to prevent any liquid leakage out of the pipe through the sensor when the corrodible membrane is pierced.

A second seal means is provided in order to prevent fouling of the inside of support 1 through liquid or solid particles coming from the outside of the pipe.

According to FIG. 1, the second seal means comprises a membrane 8 that covers the opening 9 of support 1 on the outer side of the pipe. Membrane 8 is fastened to opening 9 by any known means (sticking, crimping, ...). Piston 3 then has a pointed end 10 that can pierce membrane 8 when the piston moves towards the outside of the pipe.

Figure 2:
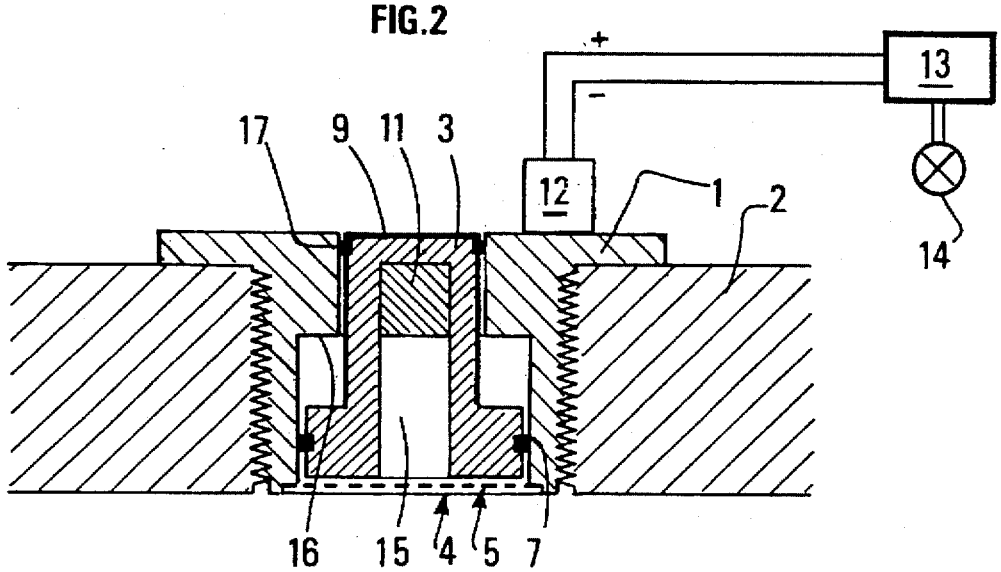
FIG. 2 is a longitudinal section of another embodiment of the invention.

According to FIG. 2, the second seal means consists of an O-ring 17 mounted on piston 3.

According to another aspect of the invention, movable means 3 can comprise a magnetized zone 11. According to FIG. 2, the magnetized zone can consist of a magnet situated at the bottom of a blind hole 15 along the axis of the piston.

According to FIG. 1, magnetized zone 11 is included in the piston itself.

The invention preferably works as follows:

When membrane 4 corrodes under the action of the cooling fluid, it breaks and the pressure difference between the inside and the outside of the circuit causes the piston to move along the longitudinal axis of the sensor, towards the outside of the pipe (the pressure in a cooling circuit being in fact higher than atmospheric pressure).

The displacement of piston 3 which, according to FIG. 1, leads to the breaking of membrane 8, brings it into a position where it rests against a shoulder 16 of support 1 forming a housing for piston 3. Piston 3 thus protrudes from the pipe or support 1. This protuberance is therefore a visual indication showing that the liquid circulating in the pipe is corroded.

In order to prevent piston 3 from returning to its initial position in the support, the zone of the support that is the closest to the shoulder can exhibit a greater section 18 in which the O-ring 7 expands when the piston comes out of its housing.

Besides, if the piston is externally covered with a coloured film 6, it will be all the more visible from the outside.

According to another aspect of the invention, piston 3 can also comprise a magnetized zone 11. A contactor 12 that can be, for example, a Reed relay known in the art, is mounted outside the pipe so as to be placed directly opposite magnetized zone 11 when the latter is also outside the pipe as a result of the outward motion of piston 3.

In this position, the magnet closes the electric circuit 13 to which the relay belongs, which activates an alarm 14 or any other indicator of the electric circuit.

Of course, other minor changes can be brought by the man skilled in the art to the sensor that has been described without departing from the scope of the present invention.

I claim:

1. A sensor for monitoring a cooling liquid circulating in a circuit of a heat exchanger comprising:

a support for mounting the sensor on a pipe of the circuit so that said liquid is in contact with at least a part of the sensor, a corrodible membrane in contact with the liquid, a visual indicator reacting to the degree of corrosion of the liquid, characterized in that the visual indicator includes a means movable outwardly relative to the pipe under the combined effect of the breaking of a corrodible membrane and a pressure difference between inside and outside of the circuit and comprising a magnetized zone, a contactor placed outside the pipe, cooperating with the magnetized zone by an interaction of a magnetic field from the magnetized zone and an electric circuit including an alarm activated when the magnetized zone is positioned opposite to the contactor, at least one seal means mounted on the movable means, and the visual indicator protruding from the pipe and/or support when said membrane is corroded and moves outwardly relative to the pipe.

2. A sensor for monitoring a cooling liquid circulating in a circuit of a heat exchanger comprising:

a support for mounting the sensor on a pipe of the circuit so that said liquid is in contact with at least a part of the sensor, a corrodible membrane in contact with the liquid, and a visual indicator reacting to the degree of corrosion of the liquid, characterized in that the visual indicator includes a means movable under the combined effect of the breaking of the corrodible membrane and of a pressure difference between inside and outside of the circuit, at least one seal means mounted on the movable means, the visual indicator protruding from the pipe and/or the support when said membrane is corroded, the piston comprises a pointed end and the second seal means is a membrane covering a opening of the piston housing that can be pierced by the pointed end of the piston when the piston moves towards the outside of the pipe.

3. A sensor as claimed in claim 2, characterized in that the movable means is at least partly covered externally with a coloured film which protrudes from the support when the membrane is corroded.

4. A sensor as claimed in claim 2, characterized in that the sensor comprises a second seal means for preventing liquid or solid particles from getting into the sensor and from hampering the motion of the movable means.

5. A sensor as claimed in claim 2, characterized in that the movable means includes a piston housed within said support and sliding in said support upon breakage of said membrane.

6. A sensor as claimed in claim 2, characterized in that the second seal means is an O-ring mounted on the piston.

7. A sensor as claimed in claim 2, characterized in that the sensor also comprises a support-grid fastened to the support between said corrodible membrane and the piston.

* * * * *